(12) United States Patent
Maruyama

(10) Patent No.: US 9,943,667 B2
(45) Date of Patent: Apr. 17, 2018

(54) GUIDE WIRE AND CATHETER ASSEMBLY

(75) Inventor: Tomoji Maruyama, Hadano (JP)

(73) Assignee: TERUMO KABUSHIKI KAISHA, Shibuya-Ku, Tokyo (JP)

(*) Notice: Subject to any disclaimer, the term of this patent is extended or adjusted under 35 U.S.C. 154(b) by 50 days.

(21) Appl. No.: 13/595,265

(22) Filed: Aug. 27, 2012

(65) Prior Publication Data
US 2012/0316433 A1 Dec. 13, 2012

Related U.S. Application Data

(63) Continuation of application No. PCT/JP2010/073435, filed on Dec. 24, 2010.

(30) Foreign Application Priority Data

Mar. 16, 2010 (JP) ................................. 2010-059894

(51) Int. Cl.
*A61B 5/05* (2006.01)
*A61M 25/09* (2006.01)
(Continued)

(52) U.S. Cl.
CPC ......... *A61M 25/09* (2013.01); *A61B 1/00071* (2013.01); *A61B 1/00087* (2013.01);
(Continued)

(58) Field of Classification Search
CPC ............ A61B 1/00071; A61B 1/00087; A61B 1/00163; A61B 1/01; A61M 2025/09133
See application file for complete search history.

(56) References Cited

U.S. PATENT DOCUMENTS 6,134,003 A * 10/2000 Tearney et al. ............... 356/479
6,445,939 B1 * 9/2002 Swanson et al. ............. 600/342
(Continued)

FOREIGN PATENT DOCUMENTS

JP H06-218060 A 8/1994
JP 2000-503237 A 3/2000
(Continued)

OTHER PUBLICATIONS

International Search Report (PCT/ISA/210) dated Mar. 29, 2011, by the Japanese Patent Office as the International Searching Authority for International Application No. PCT/JP2010/073435.
(Continued)

*Primary Examiner* — Amanda Lauritzen Moher
*Assistant Examiner* — Shahdeep Mohammed
(74) *Attorney, Agent, or Firm* — Buchanan Ingersoll & Rooney PC

(57) ABSTRACT

A guide wire includes an elongated main body possessing flexibility. The main boy is comprised of a first wire having a core member constituted by a metal material, a second wire having a core member arranged on the proximal side of the first wire and constituted by a metal material, and an optically transmissive member arranged between the first wire and the second wire, and connecting the first and second wires to each other and constituted by a substantially transparent tube shaped body. The optically transmissive member exhibits light permeability such that when light is illuminated from one direction of a lateral side thereof, the light is transmissible to the opposite side through the center axis of the main body.

19 Claims, 9 Drawing Sheets

(51) Int. Cl.
*A61B 1/01* (2006.01)
*A61B 1/00* (2006.01)

(52) U.S. Cl.
CPC ............ *A61B 1/00163* (2013.01); *A61B 1/01* (2013.01); *A61M 2025/09133* (2013.01)

(56) References Cited

U.S. PATENT DOCUMENTS

| | | | |
|---|---|---|---|
| 7,736,301 B1* | 6/2010 | Webler et al. | 600/125 |
| 2004/0067000 A1* | 4/2004 | Bates et al. | 385/7 |
| 2005/0101870 A1 | 5/2005 | Yamaguchi | |
| 2006/0106287 A1* | 5/2006 | Webler | A61B 5/0084 600/176 |
| 2006/0173381 A1 | 8/2006 | Eck | |
| 2007/0038125 A1* | 2/2007 | Kleen | A61B 5/0066 600/476 |
| 2007/0213735 A1* | 9/2007 | Saadat et al. | 606/79 |
| 2008/0228085 A1* | 9/2008 | Jenkins | A61B 1/00071 600/478 |
| 2009/0018393 A1* | 1/2009 | Dick et al. | 600/109 |
| 2009/0030277 A1* | 1/2009 | Fujimoto et al. | 600/114 |
| 2009/0048668 A1* | 2/2009 | Wilson et al. | 623/2.36 |
| 2012/0002928 A1 | 1/2012 | Irisawa | |

FOREIGN PATENT DOCUMENTS

| | | |
|---|---|---|
| JP | 2004-097286 A | 4/2004 |
| JP | 2004-344274 A | 12/2004 |
| JP | 2006-507884 A | 3/2006 |
| WO | WO 03051184 A1 * | 6/2003 ......... A61B 1/00071 |
| WO | WO 2009/009799 A1 | 1/2009 |
| WO | 20091154103 A1 | 12/2009 |

OTHER PUBLICATIONS

Machine Translation of Official Action drafted by the Japanese Patent Office on Jul. 7, 2014 in Japanese Application 2012-505460 (5 pgs).
Japanese Office Action dated Feb. 3, 2015 for corresponding Application No. 2012-505460.

* cited by examiner

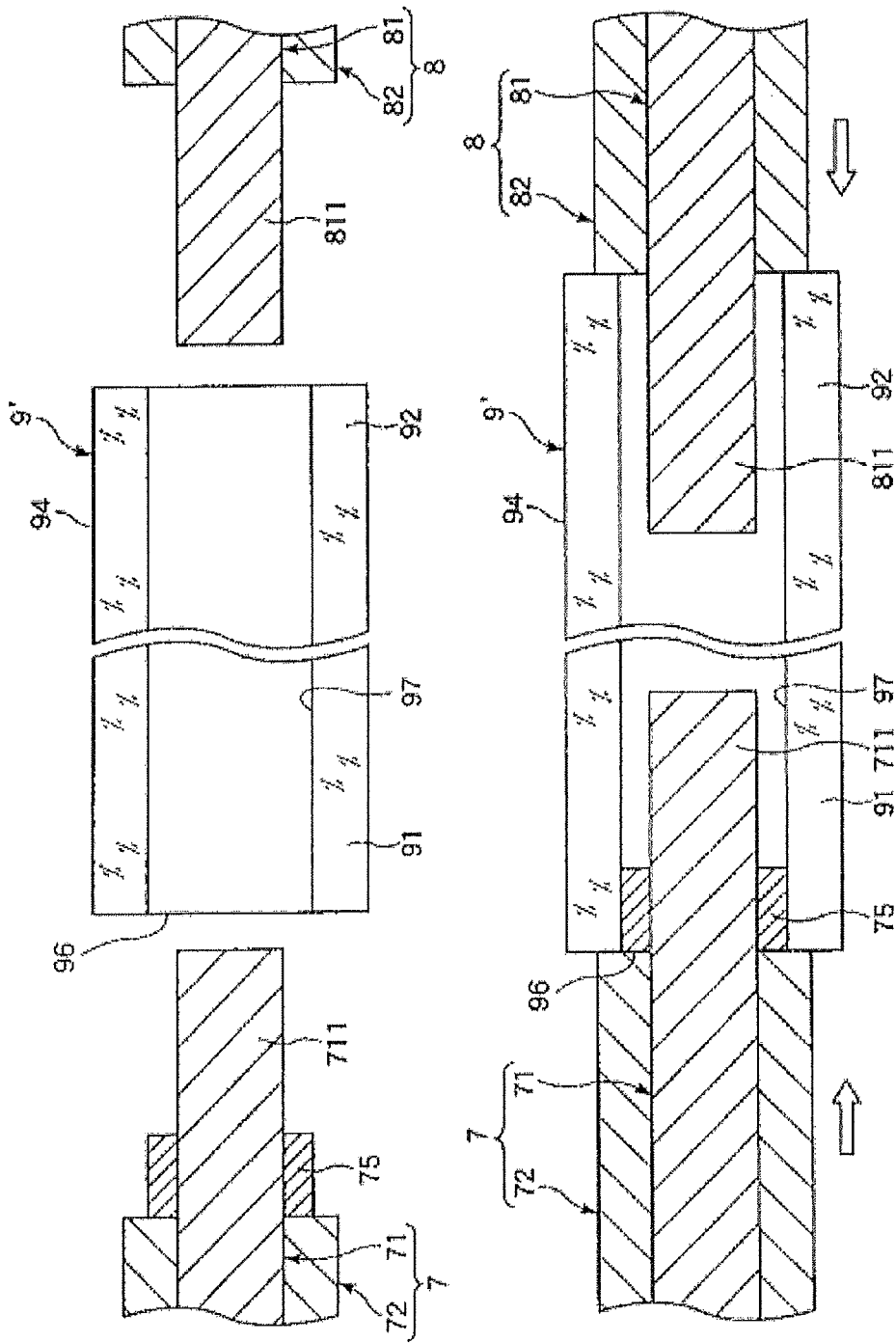

GUIDE WIRE AND CATHETER ASSEMBLY

This application is a continuation of International Application PCT/JP2010/073435 filed on Dec. 24, 2010, which claims priority to Japanese Patent Application No. 2010-059894 filed Japan on Mar. 16, 2010, the entire content of both of which is incorporated herein by reference.

TECHNICAL FIELD

The present invention generally relates to a guide wire and a catheter assembly provided with such guide wire.

BACKGROUND DISCUSSION

There has been known a catheter inserted into the inside of a living body lumen such as a blood vessel or the like and used for carrying out diagnosis of the inside of the lumen by. An example is described in Japanese Unexamined Patent Publication No. 2004-344274.

The catheter described in this document is provided with a catheter main body including a lumen, a tubular guide wire insertion portion which is installed at a distal portion of the catheter main body and into which a guide wire is inserted, and a shaft which is inserted into the lumen of the catheter main body and which includes, at a distal portion thereof, an ultrasound oscillation unit emanating ultrasound. In a state of inserting the guide wire in the guide wire insertion portion, this catheter rotates the shaft which is inserted inside the lumen of the catheter main body around the axis thereof and concurrently, moves the shaft in the proximal direction, thereby making it possible to obtain ultrasound images of a blood-vessel wall.

It is also possible for the catheter described in this patent publication to be used, depending on the procedure, in such a manner that a shaft capable of imaging a blood-vessel wall by emanating light and light-receiving the reflection light thereof is inserted in the catheter main body instead of the shaft having the ultrasound oscillation unit.

Then, in the catheter described in the patent publication, the guide wire inserted into the guide wire insertion portion includes a metal core wire existing from the past, so that in case of carrying out image acquisition optically as mentioned above, light is shut by the guide wire and there arises a shadow, so-called "back shadow", in the image caused by the aforesaid guide wire as shown in FIG. 10. Consequently, at the portion where the back shadow of the image arises, that portion becomes a blind spot and the blood-vessel wall cannot be imaged. In a situation in which, for example, a lesion portion exists at the aforesaid portion which is not imaged, there is a concern that it may be difficult to visually confirm this lesion portion.

SUMMARY

The guide wire and catheter assembly disclosed here can reliably prevent a back shadow by the guide wire from arising on the image when taking a picture of the image inside the living body lumen.

The guide wire includes an elongated main body which is flexible and possesses a center axis, the main body including an optically transmissive portion at least at a portion of the main body in a lengthwise direction of the main body, and the optically transmissive portion possessing light permeability such that when light is illuminated toward the optically transmissive portion from one direction of a lateral side of the optically transmissive portion, the light is transmitted through the optically transmissive portion to an opposite side of the optically transmissive portion through the center axis of the main body.

It is preferable for the optically transmissive portion to be arranged along the lengthwise extent of the main body. It is preferable for the optically transmissive portion to be at least partially constituted by a tube shaped body.

The main body can be comprised of a first wire connected to a distal portion of the tube shaped body and having a core member constituted by a metal material, and a second wire connected to a proximal portion of the tube shaped body and having a core member constituted by a metal material.

The first and second wires can include diameter-expanded portions whose outer diameters are expanded at the portions positioned in the tube shaped body.

The guide wire is configured as a wire which is used in a state of being inserted in a tubular insertion portion of a catheter, wherein the catheter includes a catheter main body constituted by a tube, at least a portion of whose tube wall is provided with a window portion, and into which there is inserted an elongated medical instrument provided with imaging means for imaging an aimed region by illuminating an optical signal through the window portion, with the tubular insertion portion at a distal portion of the catheter main body. The optically transmissive portion is a portion which permits passage of at least the optical signal therethrough, and the wire main body is provided with a positioning marker which is visibly confirmed under X-ray illumination when carrying out positioning with respect to the medical instrument.

A positioning marker can be positioned in the vicinity of the distal side of the optically transmissive portion. The main body preferably has a flexible portion at a distal portion thereof and the optically transmissive portion is positioned on the side more proximal than the flexible portion.

It is also preferable that the distal-most end of the optically transmissive portion is positioned 5 mm to 200 mm from the distal-most end of the main body. The length of the optically transmissive portion is preferably 100 mm or more.

The optically transmissive portion can be made of a resin material which permits passage of near-infrared light therethrough.

Also disclosed is a catheter assembly provided with the guide wire disclosed here together with a catheter. The catheter includes a catheter main body constituted by a tube, at least a portion of whose tube wall is provided with a window portion, and a tubular insertion portion at a distal end portion of the catheter main body and into which the guide wire is inserted. The catheter also includes imaging means for imaging an aimed region by illuminating or emitting an optical signal through the window portion while the guide wire is positioned in the insertion portion.

Another aspect of the disclosure here involves a guide wire usable with a catheter having a light transmitting member from which light is transmitted. The guide wire comprises an elongated main body which is flexible and possesses a longitudinally extending central axis, a distal end portion and a proximal end portion. The main body includes an intermediate portion located between the distal end portion of the main body and the proximal end portion of the main body, wherein the intermediate portion including an axial extent and a circumferential extent. At least the intermediate portion of the main body is an optically transmissive portion made of a light permeable material which allows the light from the light transmitting member directed at one side of the optically transmissive portion to enter the optically transmissive portion at the one side, intersect the longitudinally extending central axis and then exit the optically transmissive portion at an other side that is opposite the one side. The light permeable material forming the optically transmissive portion extends around the entire circumferential extent of the intermediate portion.

Another aspect of the disclosure here is a method that involves advancing a catheter in a lumen of a living body toward an aimed region, wherein the catheter is comprised of: a catheter main body possessing a tube wall surrounding a lumen and provided with a window portion; a light transmitting member configured to transmit light; and a tubular insertion portion at a distal end portion of the catheter main body. The catheter is advanced toward the aimed region while being guided along a guide wire positioned in the tubular insertion portion. The guide wire includes a main body possessing a central axis and comprising an optically transmissive portion. The method additionally involves transmitting the light from the light transmitting member along a path toward a wall of the blood vessel while simultaneously rotating and axially moving the light transmitting member, the path of the light intersecting the guide wire at spaced apart intervals during rotation of the light transmitting member, and the light transmitted by the light transmitting member passing through the window portion of the catheter main body and also passing through the optically transmissive portion of the guide wire when the path of the light intersects the optically transmissive portion, with the light passing though the optically transmissive portion of the guide wire by entering through one side of the optically transmissive portion and exiting through an opposite side of the optically transmissive portion while passing though the central axis of the guide wire.

BRIEF DESCRIPTION OF DRAWINGS

FIGS. 5(a) and 5(b) are longitudinal cross-sectional views for sequentially showing an example of a manufacturing method of the guide wire shown in FIG. 4.

DETAILED DESCRIPTION

Figure 1:
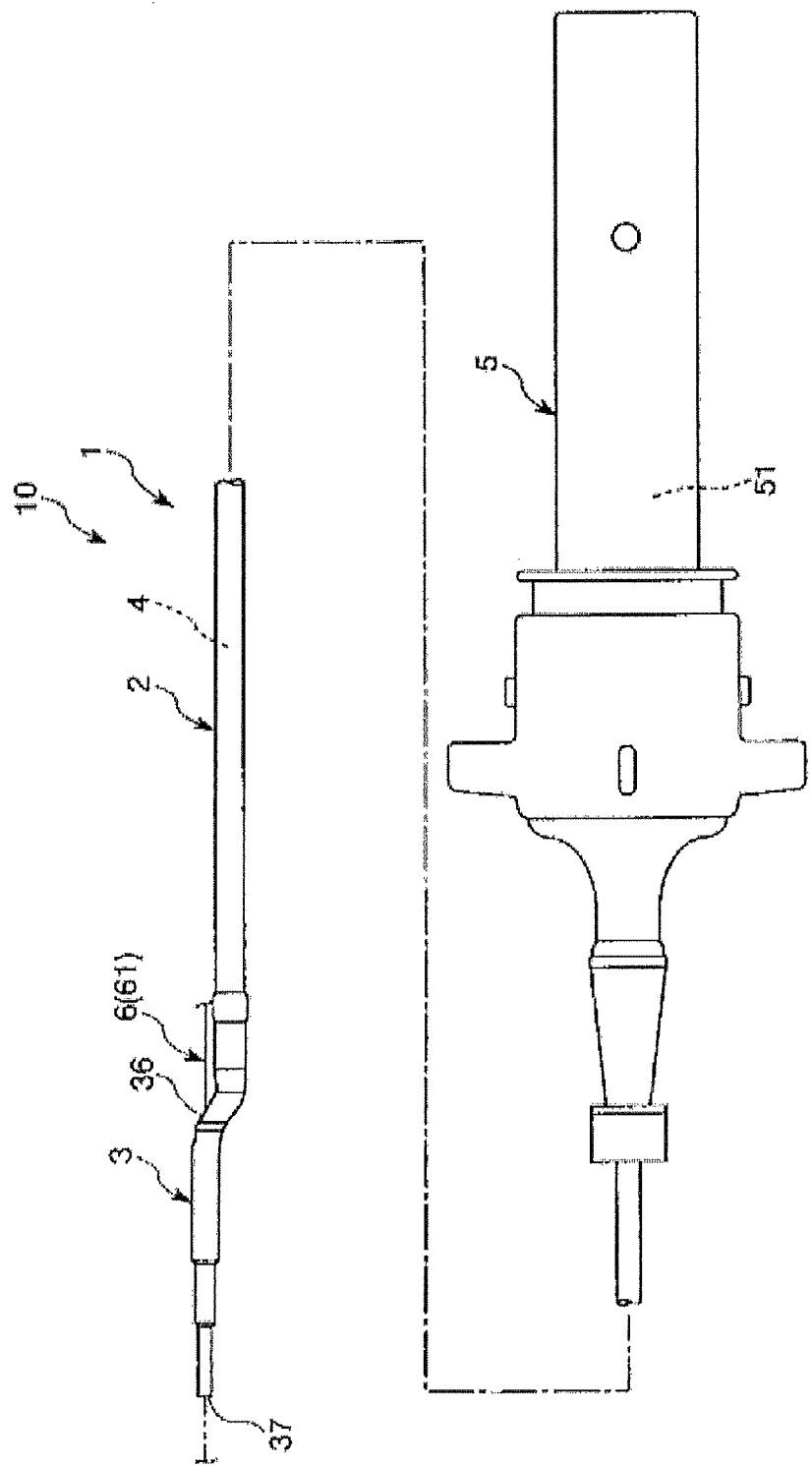
FIG. 1 is a side view of a catheter assembly disclosed here by way of example.

Set forth below with reference to the drawing figures is a detailed description of a guide wire and a catheter assembly disclosed here. FIGS. 1-7 and 9 illustrate a first embodiment serving as one example of the disclosure here will be described. For convenience of explanation, the right side in FIGS. 1-7 (and FIG. 8 as well) is referred to as the "proximal end" and the left side is referred to as the "distal end". Also, in FIGS. 4-7 (and in FIG. 8 as well), to facilitate an understanding of aspects of the guide wire, each drawing is shown schematically by shortening the length direction of the guide wire and by exaggerating the thickness direction of the guide wire, so that the ratio between the illustrated length and the illustrated thickness is largely different from the actual ratio.

Figure 9:
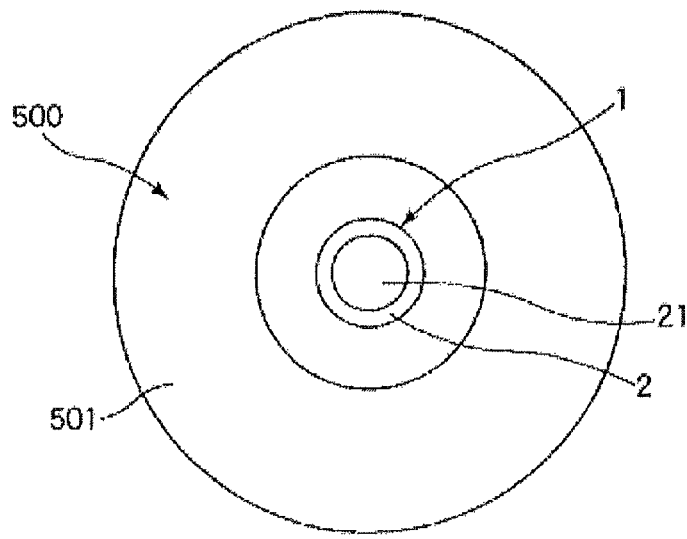
FIG. 9 is a schematic view showing a blood-vessel wall imaged by using the catheter assembly shown in FIG. 1.
Figure 10:
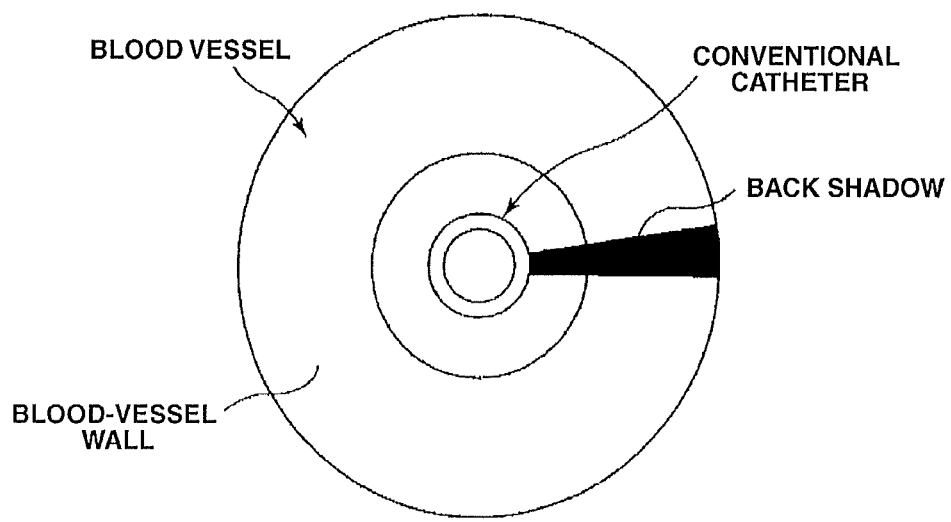
FIG. 10 is a schematic view showing a blood-vessel wall imaged by using a conventional catheter assembly.

The catheter assembly 10 shown in FIG. 1 is an assembly that includes the combination of a catheter 1 and a guide wire 6. The assembly is used in a state in which the catheter 1 and the guide wire 6 are assembled. The catheter assembly 10 is nserted into a living body lumen in this assembled state. There is no limitation on the living body-lumen in particular. A blood vessel 500 is mentioned as one example and is illustrated in FIG. 9.

The catheter 1 includes a catheter main body 2 constituted by a tube having flexibility (flexible tube), a guide wire insertion portion 3 located at a distal portion of the catheter main body 2 and into which the guide wire 6 is insertable, an elongated, linear drive shaft 4 housed inside the catheter main body 2 and movable along the lengthwise or axial direction thereof, and a connector 5 located at a proximal portion of the catheter main body 2. This catheter 1 is a catheter configured to be inserted into the inside of the blood vessel 500 in a state in which the guide wire 6 is inserted in the guide wire insertion portion 3 as mentioned above and is a so-called "rapid exchange type (short monorail type)" catheter which makes it possible to carry out the pulling-out and insertion of the guide wire 6 rather speedily.

Figure 2:
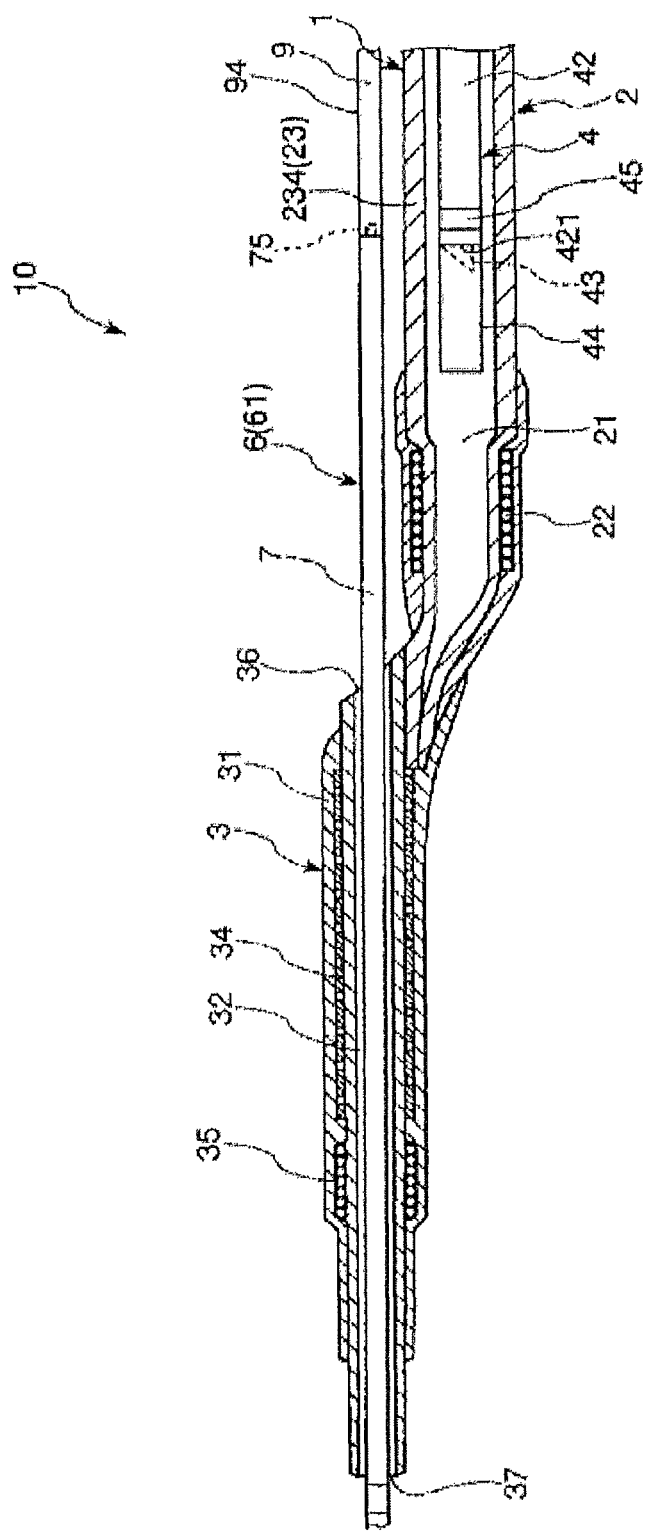
FIG. 2 is a partial longitudinal cross-sectional view for sequentially showing the use state of the catheter assembly shown in FIG. 1.
Figure 3:
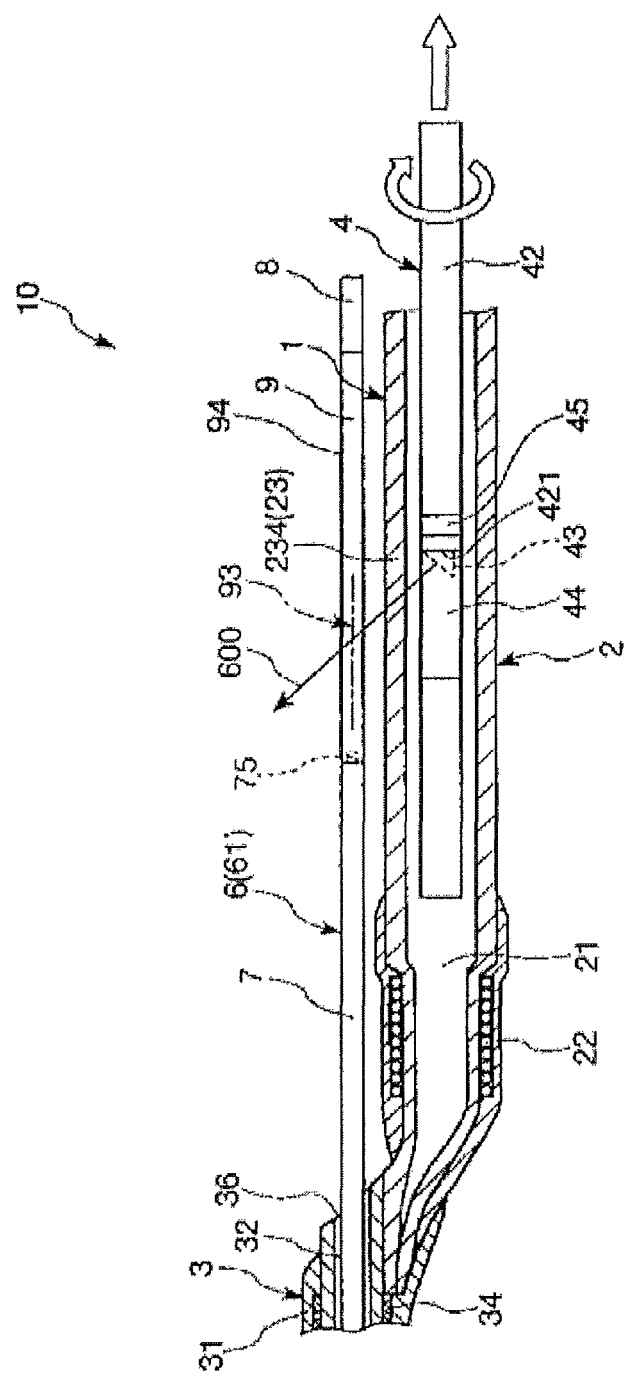
FIG. 3 is a partial longitudinal cross-sectional view for sequentially showing the use state of the catheter assembly shown in FIG. 1.

As shown in FIG. 2 and FIG. 3, the catheter main body 2 includes a lumen 21 extending along the lengthwise or axial direction of the catheter main body 2. Into the inside of this lumen 21, it is possible to insert or position a drive shaft 4 serving as a rotation drive body and discussed in more detail below. The catheter main body 2 is a body whose distal end is blocked or closed. Thus, the drive shaft 4 is prevented from protruding distally beyond the distal end of the catheter main body 2.

The catheter main body 2 includes a tube wall 23 surrounding the lumen 21. FIG. 2 and FIG. 3 show that at least a portion of the tube wall 23 of the catheter main body 2 on the distal side of the tube wall 23 constitutes or includes a window portion 234 having transparency. The catheter 1 is a catheter used in imaging by an optical signal, in particular, for an optical coherence tomography (OCT) imaging apparatus for diagnosis and for an optical frequency domain imaging (OFDI) apparatus utilizing wavelength sweep, which is an improvement type thereof. After directing a near-infrared light ray emitted from a transmission & receiving unit provided at a distal portion of the drive shaft 4 (imaging means), as will be described in more detail below, onto the biological tissue through this window portion 234, and after generating coherent light by causing the reflection light from the biological tissue to interfere with the reference light, it is possible to visualize the cross-section image of the blood vessel 500 based on the aforesaid coherent light.

Also, a coil 22 is buried in the wall portion of the catheter main body 2 at the distal end portion of the catheter main body 2. In this embodiment described by way of example, the coil 22 is constituted by a metal (for example, stainless steel) wire and helps reinforce the distal portion of the catheter main body 2 and impart elasticity to the distal portion of the catheter main body 2.

As shown in FIG. 2 and FIG. 3, the guide wire insertion portion 3 is positioned at and fixed to the distal end portion of the catheter main body 2. The guide wire insertion portion 3 possesses a tubular shape and includes a through lumen 32 through which the guide wire 6 is to be inserted. The center axis of the guide wire insertion portion 3 is eccentric with respect to the center axis of the catheter main body 2.

The guide wire insertion portion 3 includes a distal opening portion 37 whose distal end is opened and a proximal opening portion 36 whose proximal end is opened. In the illustrated embodiment, the proximal portion of the guide wire insertion portion 3 and the distal portion of the catheter main body 2 axially overlap one another and are fixed to one another. The particular fixing method is not limited. It is possible, for example, to use a method in which the axially overlapping end portions are thermally fused to each other.

A reinforcement member 34 and a marker 35 are also buried in a tube wall 31 of the guide wire insertion portion 3. The marker 35 is arranged distally of the reinforcement member 34 and possesses a contrast property.

The reinforcement member 34 possesses a tubular shape, and is made of a resin material such as, for example, polyethylene or the like. By virtue of this reinforcement member 34, when inserting the guide wire 6 through the guide wire insertion portion 3, it is possible to reliably prevent a phenomenon that the tube wall 31 of the guide wire insertion portion 3 is torn by the guide wire 6.

The marker 35 is a marker formed, for example, by spirally winding a wire made of an X-ray impermeable metal material such as platinum. By virtue of this marker 35, it is possible, under the X-ray illumination, to reliably comprehend or ascertain the position of the guide wire insertion portion 3.

There is no limitation on the constituent materials for the tube wall 23 of the catheter main body 2 and the tube wall 31 of the guide wire insertion portion 3. Examples of suitable materials that can be used to fabricate the tube wall 23 of the catheter main body 2 and the tube wall 31 of the guide wire insertion portion 3 include various kinds of thermoplastic elastomers based on styrene, polyolefin, polyurethane, polyester, polyamide, polyimide, polybutadiene, trans-polypropylene, fluoro-rubber, chlorinated polyethylene and the like, and it is possible, within these, to use one kind or a material formed by combining two kinds or more (polymer-alloy, polymer-blend, laminated product or the like).

FIG. 2 and FIG. 3 illustrate the drive shaft 4 which is a medical instrument inserted into the inside of the catheter main body 2. The drive shaft 4 includes, for example, a main body portion 42 possessing an elongated shape, a prism 43 located at a distal end 421 of the main body portion 42 and constituting an example of a transmitting portion from which a signal (light) is transmitted, and a housing 44 in which the prism 43 is housed or stored.

The main body portion 42 is constituted as a portion formed, for example, by covering the outside of an optical fiber with a multi-layer winding coil. A proximal end portion of the main body portion 4 is connected to the connector 5 and it is possible to transmit light 600 (signal) from the scanner 51 located at the connector 5, which is discussed more fully below, through the prism 43 and to receive the reflected light from the living body.

Also, a distal end portion of the main body portion 42 is provided with a sensor marker 45 serving as an example of a positioning marker on the medical instrument side which is visibly recognized when carrying out positioning with respect to the guide wire 6. The sensor marker 45 is a marker formed by installing a ring of a metal material (e.g., platinum) at the outer circumferential portion of the main body portion 42. By virtue of this sensor marker 45, it is possible to comprehend or determine the position of the distal portion of the drive shaft 4 reliably under X-ray illumination. Also, it is possible to carry out the positioning with respect to the guide wire 6 rather reliably. The positioning will be discussed in more detail below.

The prism 43 is a perpendicular prism and is fixed on the distal end 421 (distal end of optical fiber) of the main body portion 42. The method for fixing the prism is not particularly limited. An example of a fixing method is adhesion by an adhesive agent.

The housing 44 is a member which is formed in a bottomed tubular shape and which stores and protects the prism 43 located inside the housing 44. Also, the housing 44 is fixed to the distal end 421 of the main body portion 42. The method for fixing the housing 44 to the distal end 421 of the main body portion 42 is not limited, and examples of suitable methods include soldering in addition to adhesion by an adhesive agent as mentioned above.

The catheter assembly 10 includes imaging means for imaging a blood-vessel wall 501. An example of structure forming this imaging means includes the prism 43, the main body portion 42 comprised of an optical fiber covered with a spiral metal wire, and the scanner 51.

As shown in FIG. 1, a connector 5 is connectable to the proximal portion of the catheter main body 2. This connector 5 includes, for example, an optical fiber connector. It is possible for this connector to be connected to a scanner 51 for rotating, in a high-speed manner, the drive shaft 4 including an optical fiber inside the drive shaft. It is possible for the scanner 51 having such a construction to transmit an optical signal from the prism 43 through an optical fiber installed inside the main body portion 42 and to communicate with a dedicated analyzing apparatus. Then, in this communication state, it is possible to indicate an image of the blood-vessel wall 501, constructed by the analyzing apparatus for example, on a monitor.

Figure 4:
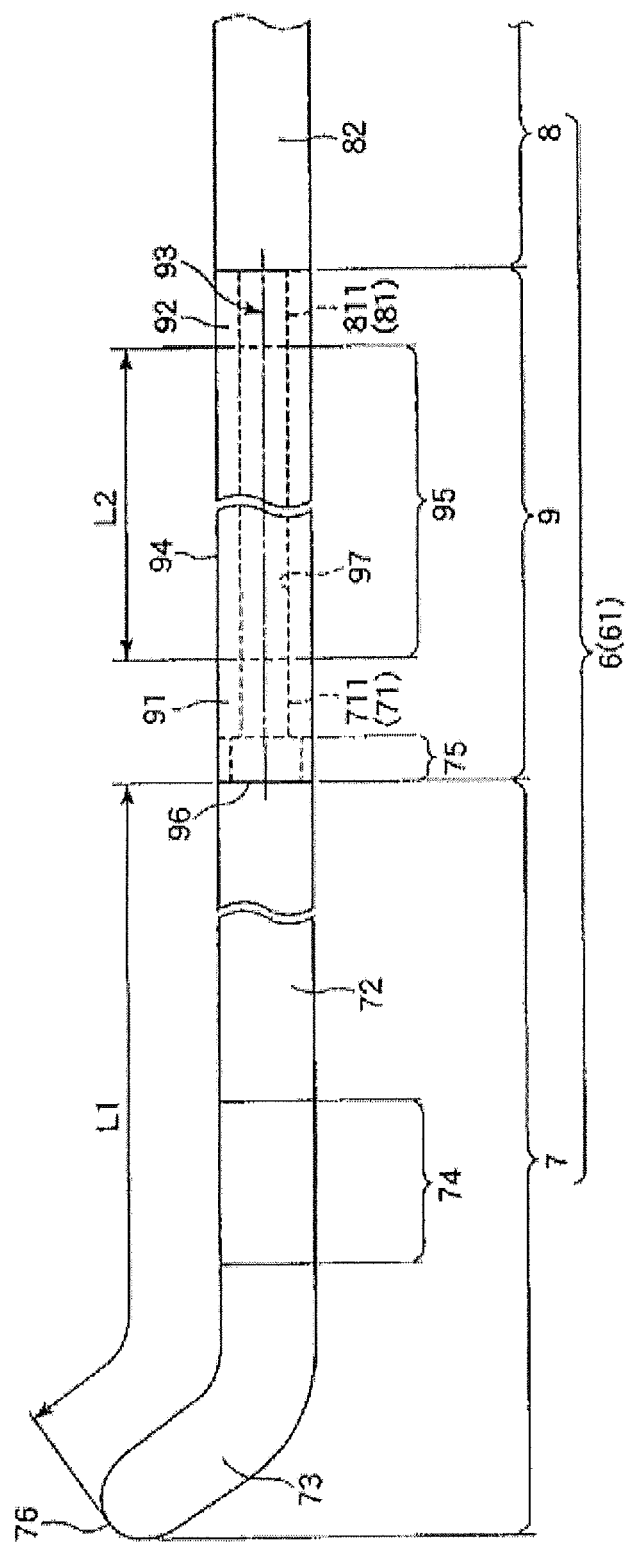
FIG. 4 is a side view of a first embodiment of a guide wire disclosed here as an example of the disclosed guide wire.

As shown in FIG. 4, the guide wire 6 is a wire including an elongated wire main body 61 having flexibility. Further, the guide wire 6 is allowed to have a coil installed so as to cover a distal portion of the wire main body 61 and constituted by forming a wire element in a spiral shape.

The guide wire 6 (wire main body 61) includes a first wire 7, a second wire 8 arranged on the proximal side of the first wire 7, and an optically transmissive member 9 which is arranged between the first wire 7 and the second wire 8 and which functions as an interlock member for interlocking or connecting together the first and second wires 7, 8. Set forth below is a description of each portion of the guide wire.

Figure 6A:
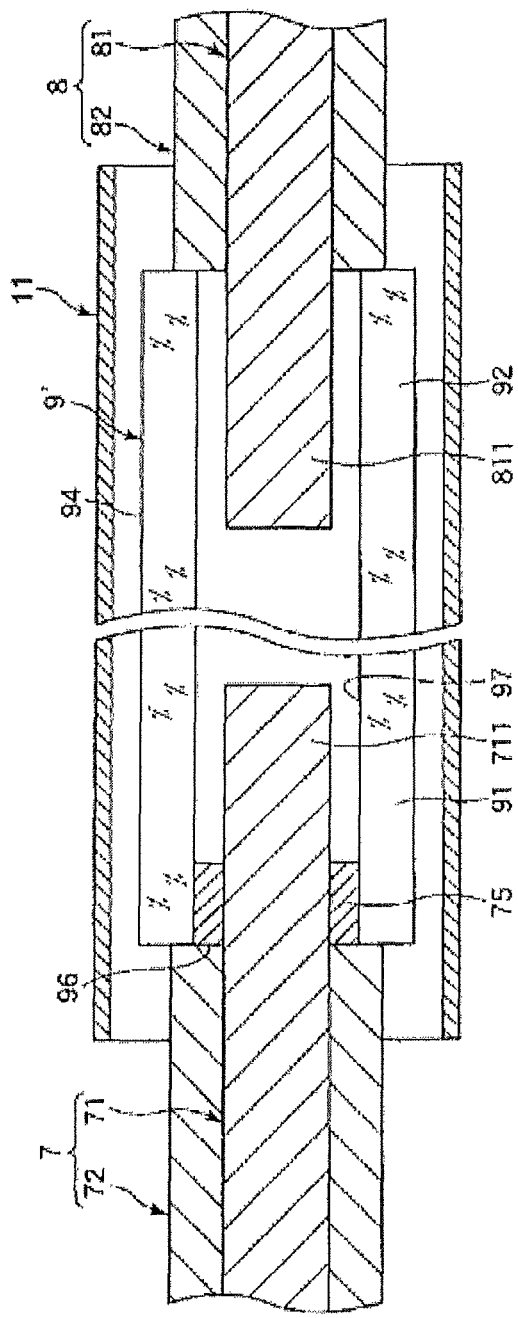
FIGS. 6(a) and 6(a) are longitudinal cross-sectional views for sequentially showing an example of a manufacturing method of the guide wire shown in FIG. 4.
Figure 6B:
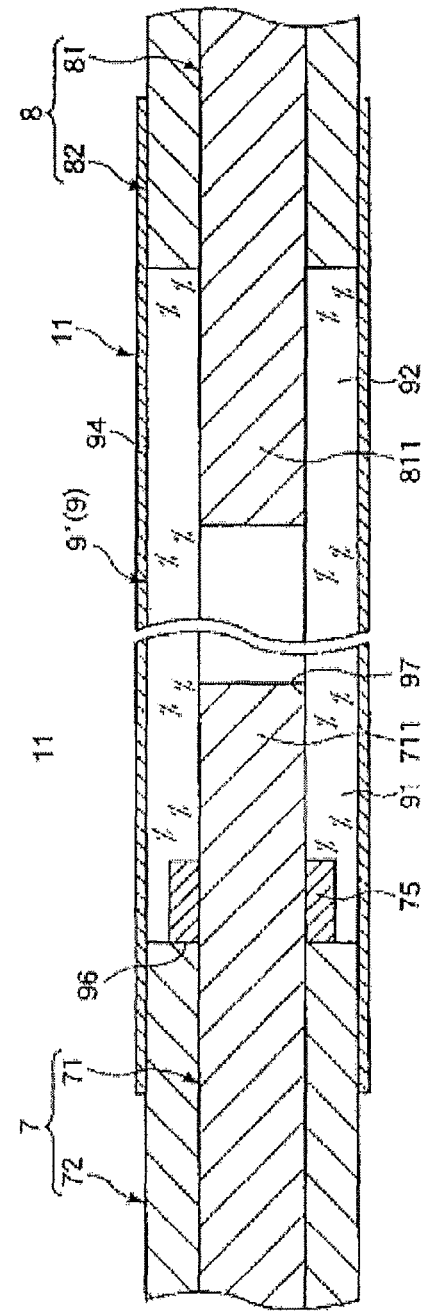
Figure 7:
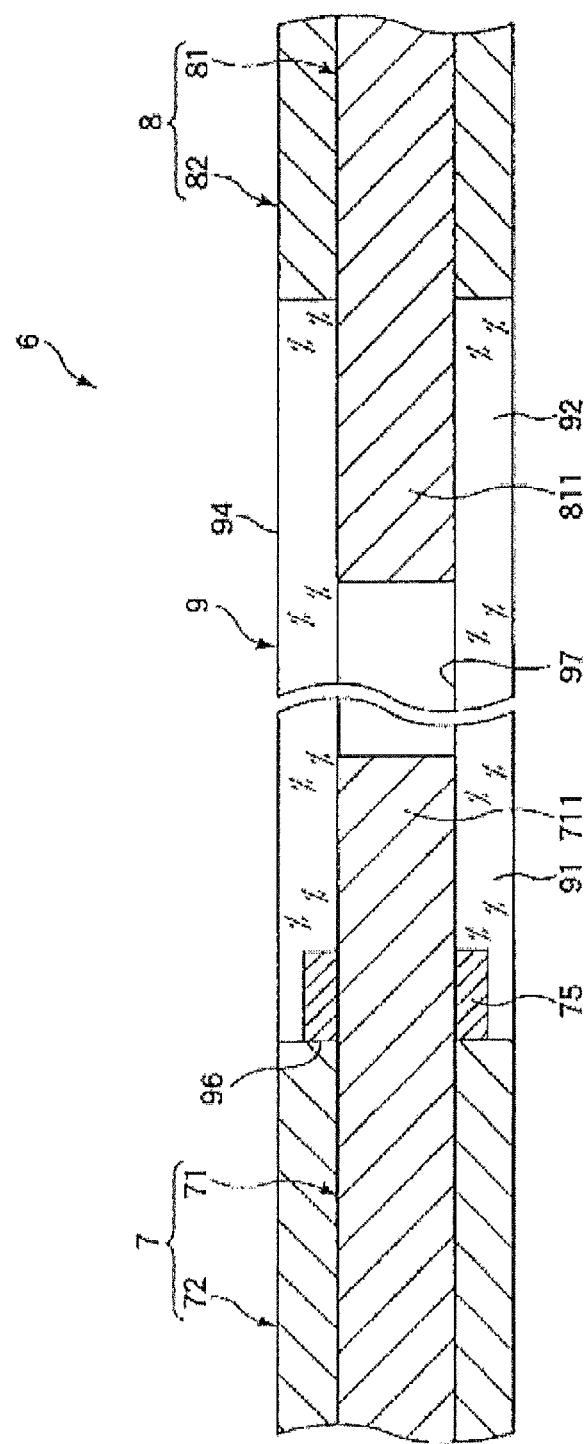
FIG. 7 is a longitudinal cross-sectional view for sequentially showing an example of a manufacturing method of the guide wire shown in FIG. 4.

As shown in FIG. 7 (similarly, also with respect to FIGS. 4 to 6), the first wire 7 includes a wire element 71 which serves as a core member and a coating layer 72 which covers the outer circumferential portion of the wire element 71. In the illustrated embodiment, the coating layer 72 extends circumferentially around the entire outer circumference of the wire core member 71 and also extends along the entire axial (longitudinal) extent of the wire core member 71, except for a proximal end portion of the wire core member 71. Also, the second wire 8 includes an wire element 81 which serves as a core member and a coating layer 82 which covers the outer circumferential portion of the wire element 81. In the illustrated embodiment, the coating layer 82 extends circumferentially around the entire outer circumference of the wire core member 81 and also extends along the entire axial (longitudinal) extent of the wire core member 81, except for a proximal end portion of the wire core member 81.

The wire elements 71 and 81 are wires having flexibility respectively. There is no limitation on the materials which can be used to form the wire elements 71, 81, and it is possible to use various kinds of metal materials and various kinds of plastics, with stainless steel, piano wire, cobalt-based alloy and the like preferably being used. It is possible for the wire element 71 and the wire element 81 to be made of identical materials or different materials.

As the material forming the element wire 71, it is also possible to use a super elastic alloy instead of the aforementioned materials. In this case, the guide wire 6 is superior both in flexibility on the distal side thereof and in rigidity on the proximal side thereof. As a result, while the guide wire 6 obtains excellent press ability and torque transmissibility and secures favorable operability, it obtains, on the distal side thereof, favorable flexibility and restoration property and exhibits improved characteristics in terms of blood vessel following capability and safety. A preferable composition of the super elastic alloy includes a Ti—Ni based alloy such as a Ti—Ni alloy containing 49 to 52 atomic % of Ni, or the like, a Cu—Zn alloy containing 38.5 to 41.5 weight % of Zn, a Cu—Zn—X alloy containing 1 to 10 weight % of X (X is at least one kind within Be, Si, Sn, Al, Ga), a Ni—Al alloy containing 36 to 38 atomic % of Al, or the like. The composition particularly preferable within those is the aforementioned Ti—Ni based alloy.

Also, it is preferable for the outer diameter of each of the wire elements 71, 81 to be 0.10 mm to 1.00 mm (0.005" to 0.038") respectively, and more preferably 0.25 mm to 0.65 mm (0.010" to 0.025").

It is possible for the coating layers 72, 82 to be formed or selected for various purposes respectively. One example involves selecting the coating layer(s) to achieve improvement in the operability of the guide wire 6 by reduction in the friction (slide resistance) of the guide wire 6 and resultant improvement in slidability.

For such a purpose, it is preferable for the coating layers 72, 82 to be respectively made of materials capable of reducing friction. Thus, the frictional resistance (slide resistance) with respect to the tube wall 31 of the guide wire insertion portion 3 of the catheter 1 which is used together with the guide wire 6 is reduced and there is improvement in slidability, and the operability of the guide wire 6 inside the guide wire insertion portion 3 becomes more favorable. Also, because the slide resistance of the guide wire 6 is reduced, when the guide wire 6 is displaced inside the guide wire insertion portion 3, it is possible to more reliably prevent a kink (bending) or a twist of the guide wire 6, in particular, a kink or a twist in the vicinity of a welded portion.

Examples of materials capable of reducing friction include a polyolefin such as polyethylene, polypropylene or the like, polyvinyl chloride, polyester (PET, PBT or the like), polyamide, polyimide, polyurethane, polystyrene, polycarbonate, a silicone resin, a fluorine base resin (PTFE, ETFE or the like), or a compound material of these.

Also, with respect to the first wire 7, a proximal end portion of the wire element 71 is exposed from the coating layer 72 (i.e., a proximal portion of the wire element 71 extends proximally beyond the proximal-most end of the coating layer 72). The exposed proximal end portion of the wire element 71 serves as a connection portion 711 inserted and connected to a distal end portion 91 of the optically transmissive member 9. In addition, with respect to the second wire 8, a distal end portion of the wire element 81 is exposed from the coating layer 82 (i.e., a distal end portion of the wire element 81 extends distally beyond the distal-most end of the coating layer 82). The exposed distal end portion of the wire element 81 serves as a connection portion 811 inserted and connected to a proximal portion 92 of the optically transmissive member 9.

As illustrated in FIGS. 5-7, a positioning marker 75 is located at the root portion of the connection portion 711 of the first wire 7. The positioning marker 75 in the illustrated embodiment is located at the proximal-most end of the coating layer 72 so that the coating layer 72 contacts the positioning marker 75. The positioning marker 75 is configured to be visibly recognizable when carrying out positioning with respect to the drive shaft 4. The positioning marker 75 is, for example, a marker in the form of an annular ring made of a metal material such as platinum which is posituioned at the outer circumferential portion of the connection portion 711 (i.e., the positioning marker 75 encircles a part of the wire element 71 which extends proximally beyond the proximal-most end of the coating layer 72).

As shown in FIG. 4, the distal end portion of the first wire 7 is a curved flexible portion 73. The curved flexible portion 73 is a portion forming a "J"-shape which is curved in one way (one direction) in the manner shown by the drawing, but it is not limited in this way. For example, it is possible to employ a portion forming a "U"-shape which is bent in one way (one direction) or a portion which is curved or bent at plural places toward opposite directions to each other. Also, it is possible to employ a first wire 7 whose distal end portion exhibits a linear shape by omitting the flexible portion 73.

Also, a marker 74 is disposed in the vicinity on the proximal side of the flexible portion 73 of the first wire 7. This marker 74 makes it possible to determine the position of the distal portion of the guide wire 6 under X-ray illumination. The marker 74 is, similar to the positioning marker 75, a marker in which a wire member made of a metal material such as platinum is installed on the coating layer 72 of the first wire 7.

The first wire 7 and the second wire 8 are interlocked with each other through the optically transmissive member 9. In this manner, the optically transmissive member 9 is configured as a member arranged in the lengthwise direction of the guide wire 6.

The optically transmissive member 9 has transparency (i.e., is permeable to the signal (light) 600 emitted from the prism 43/drive shaft 4) and is thus a member configured so that the signal (light) 600 is able to pass through the optically transmissive member 9 on one side of the member and exits the opposite side of the optically transmissive member 9, while passing though the center axis 93 of the optically transmissive member 9. That is, it is possible to see entirely through the optically transmissive member 9 along a line of sight extending from one side of the member 9 to the opposite side of the member 9 and passing through the center axis 93. The optically transmissive member 9 exhibits this transparency around its entire circumferential extent (360°) and over an axial extent extending between the proximal-most end of the first wire 7 and the distal-most end of the second wire 8. The term "transparency" as used here includes colored (coloring) transparency in addition to colorless transparency.

This optically transmissive member 9 is a tube-shaped (tubular) body composed of a light permeable material. The light permeable material forming the optically transmissive portion extends around the entire circumferential extent of the optically transmissive portion, meaning the light permeable material extends circumferentially continuously over 360°. The light permeable material also extends axially along an axial extent constituting a portion of the main body. In this disclosed example, the optically transmissive member 9 is made of an optically transmissive resin material or a glass material (see FIG. 7). The resin material used to form the optically transmissive member 9 is not particularly limited. Examples of suitable materials include a polyolefin such as polyethylene or the like, polyvinyl chloride, polystyrene, polyamide (examples: nylon 6, nylon 46, nylon 66, nylon 610, nylon 612, nylon 11, nylon 12, nylon 6-12, nylon 6-66), polyimide, polycarbonate (PC), acryl based resin, other fluorine based resin, various kinds of thermoplastic elastomers based on styrene, polyolefin, polyvinyl chloride, polyurethane or the like, epoxy resin, phenol resin, silicone resin, polyurethane or the like, or copolymers, blend compounds and polymer-alloys composed mainly of these, or the like, and within these, it is possible to use one kind or to use two kinds or more in combination. There is also no limitation on the specific type of glass material that can be used to fabricate the optically transmissive member 9. Examples of glass materials which can be used include quartz glass, non-alkali glass, soda glass, crystalline glass, potassium glass, borosilicate glass or the like. By using such a resin material or a glass material, the whole optically transmissive member 9 or a portion of the optically transmissive member 9 reliably becomes a member which possesses light permeability with respect to an optical signal illuminated or emitted by the imaging apparatus for diagnosis and specifically, which permits the passage of near-infrared light therethrough.

Also, the optically transmissive member 9 is comprised of the tube shaped body and so, when manufacturing the guide wire 6 by interlocking the first wire 7 and the second wire 8 together through the optically transmissive member 9, it is possible to relatively easily carry out the interlocking operation, that is, to relatively easily carry out the manufacture (see FIGS. 5 to 7).

When taking a picture of the image inside the blood vessel 500 (i.e., when directing light at the interior surface of the blood vessel), the light 600 reliably passes through the optically transmissive member 9 and more specifically, it is reliably inhibited or prevented from being shut or blocked. It is thus possible to relatively reliably prevent a back shadow by the guide wire 6 from arising on the image. This will be discussed further in the method of using the catheter assembly 10 described below.

The optically transmissive member 9 is positioned on the side more proximal than the flexible portion 73 and more specifically, it is not extended as far as the flexible portion 73. Thus, even if the optically transmissive member 9 is constituted by the constituent material so as to be a relatively hard member, it is possible to prevent exertion of an influence on the flexible portion 73 for which flexibility is required.

As mentioned above, the optically transmissive member 9 is arranged on the way in the lengthwise direction of the guide wire 6. That is, the optically transmissive member 9 is positioned at an intermediate portion of the guide wire 6, at a position proximal of the distal-most end of the guide wire 6 and distal of the proximal-most end of the guide wire 6. This area in which the optically transmissive member 9 is located is not limited to the particular location illustrated. As an example, it is preferable that the distance L1 from the distal end 76 of the guide wire 6 to the distal end 96 of the optically transmissive member 9 is 5 mm to 200 mm, more preferably 10 mm to 100 mm.

Also, the length L2 of the functional unit 95 of the optically transmissive member 9, with which light permeability is actually exerted or exhibited, is not limited. As an example, the length L2 is preferably 100 mm or more, more preferably 100 mm to 200 mm.

This numerical range provides a good balance between the safety of the operation (distal end flexibility) and material physical properties for back shadow reduction.

Set forth next, with reference to FIGS. 5-7, is an explanation of one example of a method of manufacturing the guide wire 6.

As shown in FIG. 5(a), a base material 9' which will become the optically transmissive member 9 is prepared, and the first wire 7 and the second wire 8 are also prepared.

By way of example, the first wire 7 and the second wire 8 can be formed by, cutting a single member made of a guide wire base material (i.e., a core member and a coating layer covering the core member) at an intermediate point (e.g., midway point) along its length, and subjecting the coating layer of each respective cut end portion to a polishing process to expose the respective core members. The respective portions where the end portion of each core member is exposed serve as the connection portion 711 of the first wire 7 and the connection portion 811 of the second wire 8 respectively. Then, it is possible to bond the positioning marker 75 to the connection portion 711 of the first wire 7 as shown in FIG. 5(a).

Next, as shown in FIG. 5(b), the connection portion 711 of the first wire 7 is inserted into the distal end portion 91 of the base material 9'. It is possible for the amount of insertion to be limited by virtue of the coating layer 72 of the first wire 7 contacting the base material 9'. Similarly, the connection portion 811 of the second wire 8 is inserted into the proximal portion 92 of the base material 9', with the insertion amount being limited by contact of the coating layer 82 of the first wire 8 with the base material 9'.

Next, as shown in FIG. 6(a), the outer periphery of the base material 9' is covered with a thermal contraction tube 11. The thermal contraction tube 11 extends over the entire axial extent of the thermal contraction tube 11. In the illustrated embodiment, the thermal contraction tube 11 also extends axially beyond the ends of the thermal contraction tube 11 to axially overlap with end portions of the coating layers 72, 82.

Then, when heating and pressurizing (squeezing) are performed in the state shown in FIG. 6(a), as shown in FIG. 6(b), the base material 9' fuses or softens, the outer diameter and the inner diameter thereof are reduced, and the inner circumferential surface 97 of the base material 9' deforms. That is, the thermal contraction tube 11 is subjected to heat and pressurization to reduce the inner and outer diameters of the thermal contraction tube 11. The deformed inner circumferential surface 97 of the thermal contraction tube 11 presses against and closely contacts the connection portion 711 of the first wire 7 and the connection portion 811 of the second wire 8 and by the frictional forces thereof, the connection portion 711 and the connection portion 811 are fixed with respect to the base material 9' as illustrated in FIG. 6(b).

Next, as shown in FIG. 7, the thermal contraction tube 11 is removed and the guide wire 6 is obtained.

Set forth next, with reference to FIGS. 2, 3 and 9, is a description of one example of method of using of the catheter assembly 10.

As shown in FIG. 2, the guide wire 6 is inserted into the guide wire insertion portion 3 of the catheter 1. The guide wire 6 is advanced (moved forward) inside the blood vessel until the distal end portion of the guide wire 6 is located in the vicinity of the aimed region of the blood vessel 500, and the catheter 1 is moved forward (while being guided by the guide wire) to the vicinity of the aimed region of the blood vessel 500 so that the catheter is indwelled. The positioning of the guide wire 6 and the drive shaft 4 is performed, while confirming the positioning marker 75 of the guide wire 6 and the sensor marker 45 of the drive shaft 4 under X-ray illumination, so that the guide wire 6 and the drive shaft 4 are positioned relative to one another such that the positioning marker 75 of the guide wire 6 and the sensor marker 45 of the drive shaft 4 are located at the same axial or longitudinal position. The positioning marker 75 of the guide wire 6 and the sensor marker 45 of the drive shaft 4 are thus located at axially or longitudinally overlapping positions in the lengthwise direction of the blood vessel 500.

Next, as shown in FIG. 3, in a state in which the axial and rotational position of the guide wire 6 is fixed, the drive shaft 4 is moved in the proximal direction while being rotated around its axis and while transmitting or emitting the signal (light) 600 toward the blood vessel wall. The signal 600 is reflected off the blood vessel wall, received by the drive shaft and processed in a known manner. An image of the blood-vessel wall 501 shown in FIG. 9 is thus obtained. During rotation of the drive shaft, including the light transmitting member 43, the path of the light transmitted by the light transmitting member 43 intersects the guide wire at spaced apart intervals. As described above, the optically transmissive member 9 is light permeable so that the signal (light) 600 from the drive shaft 4 passes through the optically transmissive member 9 and is reflected on the blood-vessel wall 501, and the reflected light passes through the optically transmissive member 9 again and is light-received by the drive shaft 4 as generally indicated in FIG. 3. In this manner, the light 600 is prevented from being blocked by the guide wire 6. Thus, when the image of the blood-vessel wall 501 is taken using the catheter assembly 10 disclosed here, it is possible to reliably prevent a back shadow of the guide wire 6 caused by the blocking from arising on the image as illustrated in FIG. 9.

Also, in the state as shown in FIG. 2, the positioning marker 75 is positioned in the vicinity of the distal side of the optically transmissive member 9. Thus, when an imaging operation which is the next operation is carried out, it is possible to take an image of the blood-vessel wall 501 rather speedily and the image thereof becomes an image in which a back shadow is prevented.

Figure 8:
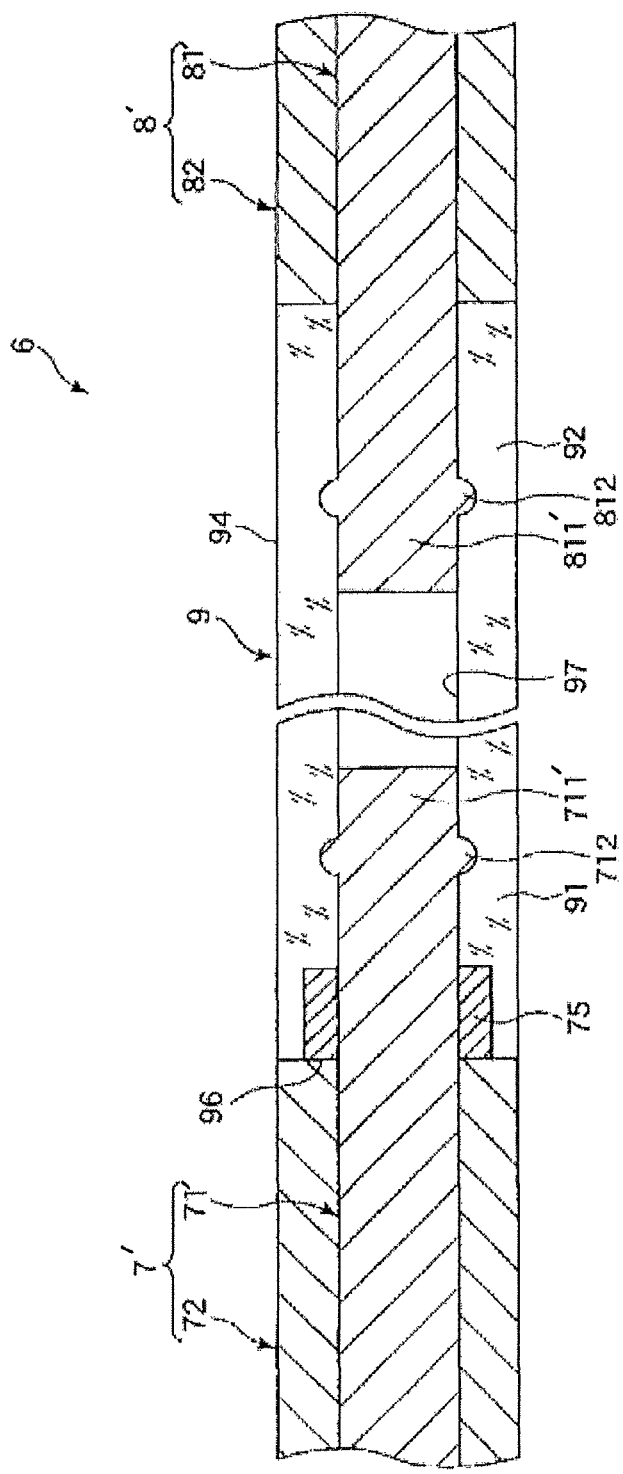
FIG. 8 is a longitudinal cross-sectional view showing a second embodiment of a guide wire disclosed here by way of further example.

FIG. 8 is a longitudinal cross-sectional view of a second embodiment of the guide wire disclosed here by way of example. Features and aspects of this second embodiment of the guide wire that are the same as the first embodiment are designated by common reference numerals, and a detailed description of such aspects and features is not repeated. The following description of the second embodiment of the guide wire, and the associated catheter assembly, focuses primarily on aspects of the guide wire and the catheter assembly differing from the embodiment described above.

This second embodiment is similar to the first embodiment, except that shapes of the respective connection portions of the first wire and the second wire are different.

As shown in FIG. 8, the connection portion 711' of the first wire 7' includes a diameter-expanded portion 712 at which the outer diameter of the first wire 7' is expanded or enlarged over a limited axial extent of the first wire 7'. Similarly, the connection portion 811' of the second wire 8' includes a diameter-expanded portion 812 at which the outer diameter of the second wire 8' is expanded or increased over a limited axial extent of the second wire 8'. The diameter-expanded portions 712, 812 engage the inner circumferential surface 97 of the optically transmissive member 9 respectively. Thus, even if an axially directed tensile force acts on the guide wire 6, it is possible to reliably prevent the connection portion 711 of the first wire 7 and the connection portion 811 of the second wire 8 from being unintentionally pulled out, or separated from, the optically transmissive member 9.

As described above, the guide wire and the catheter assembly of the present invention has been explained with respect to the exemplified embodiment shown by drawing, but the present invention is not to be limited by this, it is possible for each portion constituting the guide wire and the catheter assembly to be replaced with an arbitrary constituent which can exert a similar function. Also, an arbitrary constituent is allowed to be added.

The guide wires described above include a portion that is light permeable. But the invention is not limited inn this regard. It is possible, for example, for the entirety of the guide wire to be light permeable. In such a case, it is possible to omit a sensor marker in the guide wire.

The guide wires described above include an optically transmissive portion that is tube-shaped. It is possible for a portion, for example, whose refractive index is identical to or different from that of the optically transmissive portion, to be arranged at the hollow portion thereof.

The guide wire disclosed here by way of several embodiments representing examples of the disclosed guide wire, is a guide wire including a long wire main body having flexibility, in which the wire main body is provided with an optically transmissive portion at least at a portion in the lengthwise direction thereof, and the optically transmissive portion has such light permeability that when light is illuminated from one direction on a lateral side thereof, the light is transmissible to the opposite side through the center axis of the wire main body. By virtue of the optically transmissive portion having light permeability, more specifically, transparency, for example, in case of imaging an aimed region optically, the light passes through the transmissive portion and is reflected on the aimed region, and the reflected light passes through the transmissive portion again. In this manner, the light is prevented from being shut or blocked by the guide wire and thus, when an image of the aimed region is taken, it is possible to reliably prevent a back shadow of the guide wire caused by the blocking from arising on the image. The obtained image is thus an image which does not have a blind spot and so it is possible to carry out accurate observation with respect to the whole aimed region.

The detailed description above describes a guide wire and catheter assembly according to several embodiments disclosed by way of example. The invention here is not limited, however, to the precise embodiments and variations described above and illustrated in the drawing figures. Various changes, modifications and equivalents could be effected by one skilled in the art without departing from the spirit and scope of the invention as defined in the appended claims. It is expressly intended that all such changes, modifications and equivalents which fall within the scope of the claims are embraced by the claims.

What is claimed is:

1. A guide wire usable with a catheter having a light transmitting member from which light is transmitted, the guide wire comprising:

an elongated main body which is flexible, the main body possessing a longitudinally extending central axis, a distal end portion and a proximal end portion;

the main body including an intermediate portion located between the distal end portion of the main body and the proximal end portion of the main body, the intermediate portion including an axial extent and a circumferential extent;

at least the intermediate portion of the main body being an optically transmissive portion made of a light permeable material which allows light from the light transmitting member directed at one side of the optically transmissive portion to enter the optically transmissive portion at the one side, intersect the longitudinally extending central axis and then exit the optically transmissive portion at an other side that is opposite the one side;

a portion of the main body positioned immediately adjacent a proximal side of the optically transmissive portion being not hollow and a portion of the main body positioned immediately adjacent a distal side of the optically transmissive portion being not hollow;

wherein the portion of the main body positioned adjacent the proximal side of the optically transmissive portion includes a first connection portion;

wherein the portion of the main body positioned adjacent the distal side of the optically transmissive portion includes a second connection portion;

wherein the first connection portion and the second connection portion are configured to be received within a proximal end portion and a distal end portion, respectively, of the optically transmissive portion;

wherein the light permeable material forming the optically transmissive portion extends around the entire circumferential extent of the intermediate portion;

wherein the optically transmissive portion includes the distal end portion being connected to a first wire and the proximal end portion being connected to a second wire;

wherein the optically transmissive portion is an optically transmissive tubular member that connects the first wire and the second wire to one another, the distal end portion of the optically transmissive tubular member axially overlapping a proximal end portion of the first wire, and the proximal end portion of the optically transmissive tubular member axially overlapping a distal end portion of the second wire; and wherein the proximal end portion of the first wire includes an enlarged diameter portion at which an outer diameter of the first wire is enlarged relative to portions of the first wire on axially opposite sides of the enlarged diameter portion of the first wire so as to engage an inner circumferential surface of the optically transmissive tubular member, the enlarged diameter portion of the first wire being disposed a first axial distance from a proximal end of the first wire, the enlarged diameter portion of the first wire extending a second axial distance along the first wire, the second axial distance being less than the first axial distance, and wherein the distal end portion of the second wire includes an enlarged diameter portion at which an outer diameter of the second wire is enlarged relative to portions of the second wire on axially opposite sides of the enlarged diameter portion of the second wire so as to engage an inner circumferential surface of the optically transmissive tubular member, the enlarged diameter portion of the second wire being disposed a first axial distance from a distal end of the second wire, the enlarged diameter portion of the second wire extending a second axial distance along the second wire, the second axial distance being less than the first axial distance, the distal end portion of the optically transmissive tubular member contacting the enlarged diameter portion of the first wire and the portions of the first wire on axially opposite sides of the enlarged diameter portion of the first wire, and the proximal end portion of the optically transmissive tubular member contacting the enlarged diameter portion of the second wire and the portions of the second wire on axially opposite sides of the enlarged diameter portion of the second wire.

2. The guide wire according to claim 1, further comprising a positioning marker located between a proximal-most end of the optically transmissive portion and a distal-most end of the optically transmissive portion.

3. The guide wire according to claim 1, wherein the enlarged diameter portion of the first wire has a proximal edge and a distal edge, a maximum diameter of wherein the enlarged diameter portion of the first wire being disposed midway between the proximal edge and the distal edge of wherein the enlarged diameter portion of the first wire.

4. The guide wire according to claim 1, wherein the enlarged diameter portion of the first wire has a semicircular configuration.

5. The guide wire according to claim 1, wherein the light permeable material of which the optically transmissive portion is made is a resin material or glass.

6. The guide wire according to claim 5, wherein the optically transmissive portion is made of a resin material which permits passage of near-infrared light therethrough.

7. A guide wire comprising:

an elongated main body which is flexible and possesses a center axis;

the main body including an optically transmissive portion at least at a portion of the main body in a lengthwise direction of the main body, the optically transmissive portion possessing light permeability such that when light is illuminated toward the optically transmissive portion from one direction of a lateral side of the optically transmissive portion, the light is transmitted through the optically transmissive portion to an opposite lateral side of the optically transmissive portion through the center axis of the main body;

wherein the main body comprises a first wire connected to a distal portion of the optically transmissive portion and a second wire connected to a proximal portion of the optically transmissive portion;

wherein the first wire includes a distal connection portion and the second wire includes a proximal connection portion;

wherein the distal connection portion of the first wire is configured to be received within a distal end portion of the optically transmissive portion;

wherein the proximal connection portion of the second wire is configured to be received within a proximal end portion of the optically transmissive portion; and wherein the distal connection portion of the first wire includes a diameter-expanded portion at which an outer diameter of only an axially limited portion of the first wire is enlarged, the diameter-expanded portion of the distal connection portion of the first wire being disposed a first axial distance from a proximal end of the first wire, the diameter-expanded portion of the distal connection portion of the first wire extending a second axial distance along the first wire, the second axial distance being less than the first axial distance, and the proximal connection portion of the second wire includes a diameter-expanded portion at which an outer diameter of only an axially limited portion of the second wire is enlarged, the diameter-expanded portion of the proximal connection portion of the second wire being disposed a first axial distance from a distal end of the second wire, the diameter-expanded portion of the proximal connection portion of the second wire extending a second axial distance along the second wire, the second axial distance being less than the first axial distance, the diameter-expanded portion of the first wire and the diameter-expanded portion of the second wire being positioned in the optically transmissive portion.

8. The guide wire according to claim 7, wherein the optically transmissive portion is arranged along a lengthwise extent of the main body.

9. The guide wire according to claim 7, wherein a distal portion of the main body is a flexible portion, and the optically transmissive portion is positioned proximal of the flexible portion.

10. The guide wire according to claim 7, wherein a distal-most end of the optically transmissive portion is positioned within 5 mm to 200 mm from a distal-most end of the main body.

11. The guide wire according to claim 7, wherein the optically transmissive portion possesses a length of 100 mm or more.

12. A catheter assembly comprising:
the guide wire according to claim 7; and
a catheter including a tubular catheter main body possessing a tube wall surrounding a lumen, at least a portion of the tube wall being provided with a window portion, the catheter also including a tubular insertion portion at a distal end portion of the catheter and into which the guide wire is insertable;
the catheter includes imaging means for imaging an aimed region of a blood vessel by directing an optical signal through the window portion along a path while the guide wire is positioned in the insertion portion at a position such that the path passes through the optically transmissive portion of the guide wire.

13. The guide wire according to claim 7, wherein the diameter-expanded portion of the distal connection portion has a proximal edge and a distal edge, a maximum diameter of the diameter-expanded portion of the distal connection portion being disposed midway between the proximal edge and the distal edge of the diameter-expanded portion of the distal connection portion.

14. The guide wire according to claim 7, wherein the enlarged diameter portion of the distal connection portion has a semi-circular configuration.

15. The guide wire according to claim 7, wherein the optically transmissive portion is at least partially constituted by a tube shaped body.

16. The guide wire according to claim 15, wherein the first wire is connected to a distal portion of the tube shaped body and comprises a core member constituted by a metal material and wherein the second wire is connected to a proximal portion of the tube shaped body and comprises a core member constituted by a metal material.

17. The guide wire according to claim 7, wherein the guide wire is configured to be inserted in a tubular insertion portion at a distal portion of a tubular catheter main body of a catheter having a tube wall provided with a window portion and surrounding an interior, and in which is positioned an elongated medical instrument provided with imaging means for imaging an aimed region by directing an optical signal through the window portion;

the optically transmissive portion is a portion configured to permit transmission of at least the optical signal; and the main body is provided with a positioning marker which is visible under X-ray illumination when carrying out positioning with respect to the medical instrument.

18. The guide wire according to claim 17, wherein the positioning marker is positioned on a distal side of the optically transmissive portion.

19. A method comprising:
providing a guide wire usable with a catheter having a light transmitting member from which light is transmitted, the guide wire comprising: an elongated main body which is flexible, the main body possessing a longitudinally extending central axis, a distal end portion and a proximal end portion; the main body including an intermediate portion located between the distal end portion of the main body and the proximal end portion of the main body, the intermediate portion including an axial extent and a circumferential extent; at least the intermediate portion of the main body being an optically transmissive portion made of a light permeable material which allows light from the light transmitting member directed at one side of the optically transmissive portion to enter the optically transmissive portion at the one side, intersect the longitudinally extending central axis and then exit the optically transmissive portion at an other side that is opposite the one side; a portion of the main body positioned immediately adjacent a proximal side of the optically transmissive portion being not hollow and a portion of the main body positioned immediately adjacent a distal side of the optically transmissive portion being not hollow; wherein the portion of the main body positioned adjacent the proximal side of the optically transmissive portion includes a first connection portion; wherein the portion of the main body positioned adjacent the distal side of the optically transmissive portion includes a second connection portion; wherein the first connection portion includes an enlarged diameter portion at which an outer diameter of the first connection portion is enlarged relative to portions of the first connection portion on axially opposite sides of the enlarged diameter portion of the first connection portion, the enlarged diameter portion of the first connection portion being disposed a first axial distance from a proximal end of the first connection portion, the enlarged diameter portion of the first connection portion a second axial distance along the first connection portion, the second axial distance being less than the first axial distance, and wherein a distal end portion of the second connection portion includes an enlarged diameter portion at which an outer diameter of the second connection portion is enlarged relative to portions of the second connection portion on axially opposite sides of the enlarged diameter portion of the second connection portion, the enlarged diameter portion of the second connection portion being disposed a first axial distance from the distal end of the second connection portion, the enlarged diameter portion of the second connection portion extending a second axial distance along the second connection portion, the second axial distance being less than the first axial distance, wherein the first connection portion and the second connection portion are configured to be received within a proximal end portion and a distal end portion, respectively, of the optically transmissive portion; and wherein the light permeable material forming the optically transmissive portion extends around the entire circumferential extent of the intermediate portion;

advancing the catheter in a lumen of a living body toward an aimed region in the lumen, the catheter being comprised of: a catheter main body possessing a tube wall surrounding a lumen and provided with a window portion; a light transmitting member configured to transmit light; and a tubular insertion portion at a distal end portion of the catheter main body;

the catheter being advanced toward the aimed region while being guided along the guide wire positioned in the tubular insertion portion; and transmitting the light from the light transmitting member along a path toward a wall of the blood vessel while simultaneously rotating and axially moving the light transmitting member, the path of the light intersecting the guide wire at spaced apart intervals during rotation of the light transmitting member, the light transmitted by the light transmitting member passing through the window portion of the catheter main body and also passing through the optically transmissive portion of the guide wire when the path of the light intersects the optically transmissive portion, the light passing through the optically transmissive portion of the guide wire by entering through one lateral side of the optically transmissive portion and exiting through an opposite lateral side of the optically transmissive portion while passing through the central axis of the guide wire.

* * * * *